United States Patent [19]

Richardson et al.

[11] 4,455,371
[45] Jun. 19, 1984

[54] OXALATE OXIDASE COMPOSITION FOR ASSAY OF OXALATE

[75] Inventors: Keith E. Richardson, Columbus; David M. Obzansky, Westerville, both of Ohio

[73] Assignee: The Ohio State University Research Foundation, Columbus, Ohio

[21] Appl. No.: 354,303

[22] Filed: Mar. 3, 1982

[51] Int. Cl.$^3$ .................... C12Q 1/26; C12Q 1/28; C12N 9/02
[52] U.S. Cl. ........................... 435/25; 435/28; 435/189; 435/815
[58] Field of Search ............... 435/25, 189, 814, 815, 435/816

[56] References Cited

PUBLICATIONS

Robertson et al., Aspects of the Analysis of Oxalate in Urine-a Review, Scund. J. Urol. Nephrol. (Supp.)53, 85–95, (1980).
Hodgkinson, A., Clinical Chemistry, 16(7), 547–577, (1970).
Chiriboga, J., Biochemical and Biophysical Research Communications, 11 277, (1963).
Chiriboga, J., Archives of Biochemistry and Biophysics 116, 516–523, (1966).
Sugiura, et al., Chem. Pharm. Bull., 27(9), 2003–2007, (1979).
Laker et al., Clinical Chemistry, 26(7), 827–830, (1980).
Datta et al., Biochem. Biophys. Acta. 17, 602, (1955).
Yriberri et al., Clinical Chemistry, 26(7), 881–884, (1980).
Kobos et al., Analytica Chimica. Acta. 121, 111–118, (1980).
Gochman et al., Clinical Chemistry, 18(9), 943–950, (1972).

*Primary Examiner*—David M. Naff
*Attorney, Agent, or Firm*—Millard & Cox

[57] ABSTRACT

An oxalate oxidase can be extracted from the stems of beet by homogenizing the beet, filtering, centrifuging the filtrate, precipitating the oxalate oxidase containing fraction with acetone, dissolving the precipitate in taurodeoxycholic acid, dialyzing the solution and column chromatography. Unlike prior art oxalate oxidase compositions, the instant composition is relatively insensitive to sodium chloride and is well adapted to rapid and inexpensive oxalate assay in body fluids. The composition is inactive on almost all body fluid components other than oxalate, the only significant interfering component being ascorbate, and this ascorbate is readily removed by treatment with acid ferric chloride prior to the oxalate oxidase assay procedure, the ferric ion being thereafter removed by a cation exchange resin.

23 Claims, 6 Drawing Figures

OXALATE OXIDASE COMPOSITION FOR ASSAY OF OXALATE

This invention was developed in part by the U.S. Public Health Service, National Institutes of Health Grant No. AM-12960 and the U.S. government may have certain rights in the invention pursuant to this grant.

BACKGROUND OF THE INVENTION

Oxalic acid and its salt are produced during the normal metabolism of mammals, including human beings. Although a healthy mammal breaks down or excretes sufficient oxalate to avoid excessive accumulation of oxalate in the tissues, a number of disease states are known to be associated with malfunctions of oxalate metabolism. Firstly, about 200,000 people have to be hospitalized each year in the United States for the treatment of kidney stones and about 70% of these stones are comprised wholly or partially of oxalic acid. A much smaller number of people are afflicted with primary hyperoxaluria, a genetic metabolic disorder in which oxalate is deposited in the kidneys. Nephrolithiasis and nephrocalcinosis are usually present in patients suffering from this condition before the age of 5 and 80% of the patients die before reaching the age of 20. Secondary hyperoxaluria, having similar effects but not due to a genetic disorder, has been reported following ileal resection and jejunoileal shunt procedures, and in patients suffering from Chron's disease, diabetes mellitus, cirrhosis, pyridoxine deficiency and sarcoidosis, or in patients who have undergone methoxyfluothane anesthesia. The same complications occur in the small number of humans, and probably much larger number of household pets, who are accidentally poisoned with ethylene glycol, a common constituent of automobile radiator antifreeze. Although ethylene glycol itself is not poisonous, it is rapidly oxidized within the mammalian body to a number of oxidation products including the highly-poisonous oxalic acid. Finally, excessive oxalate excretion is frequently a complication in patients suffering from steatorrhea.

In view of the variety of clinical conditions known to be associated with malfunctions in oxalate metabolism, physicians and other medical personnel frequently require a reliable and accurate method for the measurement of oxalate in body fluids. Such oxalate assays are normally made on urine, because, in many of the aforementioned conditions, oxalate levels in blood serum are within normal ranges. The mere detection of oxalate crystals in urine is of little or no diagnostic significance, since patients with normal oxalate metabolism may also produce such crystals in the urine, as described in:

Howanitz, P. J. and Howanitz, J. H., in *Todd-Sanford-Davidsohn-Clinical Diagnosis and Management by Laboratory Methods,* J. B. Henry, W. B. Saunders Co., Philadelphia, Pa., 16th Edn.; and Hodgkinson, A., *Oxalic Acid in Biology and Medicine,* Academic Press, New York, N.Y., 1978.

Most prior art methods for measuring oxalate in urine and other body fluids require the isolation of the oxalate by a precipitation, solvent extraction or ion-exchange absorption; see, for example:

Hodgkinson, A. Determination of Oxalic acid in Biological Material, Clin. Chem. 16 (7), 547-557 (1970).

Following the isolation of the oxalate, quantitative assay thereof is completed by colorimetry, fluorometry, gas-liquid chromatography or isotope dilution techniques. Because many of the oxalate isolation techniques used in these analytical methods are not quantitative, it is normally necessary to correct for the low recovery of oxalate by adding a $^{14}C$-labeled oxalic acid internal standard, which further complicates the analytical method. All these methods are laborious, and consequently expensive because of the amount of skilled laboratory technician time which must be employed, and none of them are suited to the use of automatic analyzers.

More recently, enzymatic methods for measuring oxalate have been developed using either oxalate decarboxylase (EC 4.1.1.2. according to the enzyme nomenclature system of the International Union of Biochemists) or oxalate oxidase (EC 1.2.3.4) as the enzyme. Oxalate decarboxylase converts oxalate to carbon dioxide and formate, and the resultant carbon dioxide can be measured manometrically, by the pH change in a carbon dioxide trapping buffer or the color change in a pH indicator buffer. However, whatever method of carbon dioxide assay is adopted, the time required for diffusion and equilibration of carbon dioxide is much longer than is desirable for a rapid analytical method.

Alternatively, the formate can be assayed with formate dehydrogenase (EC 1.2.1.2.) in an NAD/NADH coupled reaction, as described in:

Costello, J. Hatch, M. and Bourke, E., An enzymic method for the spectrophotometric determination of oxalic acid, J. Lab. Clin. Med. 87(5), 903-908 (1976); and Yriberri, J. and Posten, LS., A semi-automatic enzymic method for estimating urinary oxalate, Clin. Chem. 26(7), 881-884 (1980).

This method is cumbersome and time-consuming because oxalate decarboxylase and formate dehydrogenase differ in optimum pH so that a pH adjustment is necessary during the analysis.

Oxalate oxidases produce two moles of carbon dioxide and one mole of hydrogen peroxide from each mole of oxalate. The oxalate oxidases used in prior art analytical methods have been obtained from moss and barley seedlings, as described in:

Datta, P. K. and Meeuse, B. J. D., Moss oxalic acid oxidase-a flavoprotein. Biochim. Biophys. Acta. 17, 602(1955);

Chiriboga, J., Some properties of an oxalic oxidase purified from barley seedlings, Biochem. Biophys. Res. Commun. 11, 277-282 (1963); and Chiriboga, J. Purification and properties of oxalic acid oxidase. Arch. Biochem. Biphys., 116, 516-523, (1966).

The hydrogen peroxide produced by the action of the oxalate on oxalate may be quantitatively determined by reacting it with the chromogen 3-methyl-2-benzothiazolinone (MBTH) and N,N-dimethylaniline (DMA) in the presence of a peroxidase, such as horseradish peroxidase.

The analytical methods based upon oxalate oxidase from moss and barley seedlings are probably the most convenient oxalate assay methods discovered to date, but they are still subject to two major disadvantages. Firstly, the raw material must be specially grown or prepared prior to the isolation of the oxalate oxidase. The mosses used only grow wild (it is apparently not economical to cultivate them commercially for this purpose) and the supply of moss is thus subject to all the vagaries associated with the gathering of a wild product. Although barley is of course readily available, barley seedlings are not a commercial product and the barley must be germinated especially for producing the enzyme. In view of the relatively low yield of enzyme from the moss and barley seedlings, the gathering or production of the raw material represents a considerable problem. Secondly, the oxalate oxidases from moss and barley seedlings are strongly inhibited by sodium, chloride and other common water-soluble ions which are normally present in body fluids, especially urine. Thus, if such oxalate oxidase analytical methods are to be used for the analysis of oxalate in body fluid, either substantial errors due to the presence of the interfering ions must be accepted, or elaborate pretreatment of the body fluid is necessary to remove the interfering ions before the body fluids are analyzed.

Thus, there is at present no simple, inexpensive and accurate method of assaying oxalate in body fluids. This need is well-recognized by those skilled in the art; for example, despite the plethora of oxalate assay methods described in the literature, the National Institutes of Health a few years ago awarded three contracts for the development of rapid and accurate oxalate assays. It is widely believed that the number of oxalate assays requested by physicians is considerably reduced because the existing assays are so time-consuming, costly and unreliable in their results, and that if a simple, quick and inexpensive oxalate assay method could be provided, far more oxalate tests would be performed, with consequent improvement in the diagnosis and treatment of conditions related to malfunction of oxalate metabolism.

Accordingly, this invention seeks to provide a relatively quick simple and inexpensive method for the assay of oxalate, especially in biological fluids.

SUMMARY OF THE INVENTION

It has been discovered that an oxalate oxidase can be exacted from the stems of beets and that this oxalate oxidase has properties which render it highly suitable for the assay of oxalate in body fluids. By an extraction technique described below, the beet stems can be treated to produce an oxalate oxidase composition or preparation having an activity of at least about 5 units/mg. of protein in the composition. The oxalate oxidase which is the active ingredient of such compositions has an optimum pH of about 5.7, an oxidase activity on citrate of only about 2% of its oxidase activity on oxalate, has substantially no oxidase activity on L-ascorbate, glyoxylate, glycolate, $\beta$-hydroxypyruvate, $\alpha$-ketoglutarate or succinate and is not substantially inhibited by 1.0 mM sodium chloride solution.

To extract the oxalate oxidase from the beet stems, the beet stems are first finally divided in an aqueous solution substantially isotonic with the cells in the stems. The resultant solution (actually more in the nature of a pulp) is then filtered through a coarse filler, such as cheesecloth, and the filtrate centrifuged until a precipitate forms. The resultant precipitate is suspended in an aqueous sugar solution, to which is added a water-miscible organic solvent, preferably acetone. The addition of the organic solvent causes the formation of a precipitate containing the oxalate oxidase, and this precipitate is then dissolved in an aqueous solution of taurodeoxycholic acid, dialyzed against a buffer solution having a pH of about 5.7 to about 6.8 and the dialyzed solution finally chromatographed by solid/liquid chromatography using a buffer of pH about 5.7 as the liquid phase.

The invention also provides a method for estimating oxalate in a liquid, this method comprising adding to the liquid an oxalate oxidase having an optimum pH of about 5.7, an oxidase activity on citrate of only about 2% of its oxidase activity on oxalate, having substantially no oxidase activity on L-ascorbate, glyoxylate, glycolate, $\beta$-hydroxypyruvate, $\alpha$-ketoglutarate or succinate and not being inhibited by 1.0 mM sodium chloride, thereby converting oxalate and oxygen present in the liquid to hydrogen peroxide and carbon dioxide, and assaying at least one of the oxalate and oxygen consumed, or the hydrogen peroxide and carbon dioxide produced by the oxalate oxidase, thereby determining the original concentration of the oxalate in the liquid.

The term "units" as used herein with reference to the oxidase activity of oxalate oxidases refers to the standard International Unit of such activity, which is defined as that quantity of oxidase which will use one micromole of molecular oxygen per minute at 37° C. in 51 mM phosphate buffer of pH 5.7 containing 3.5 mM flavin mononucleotide and 5 mM oxalic acid.

DETAILED DESCRIPTION OF THE INVENTION

Figure 1:
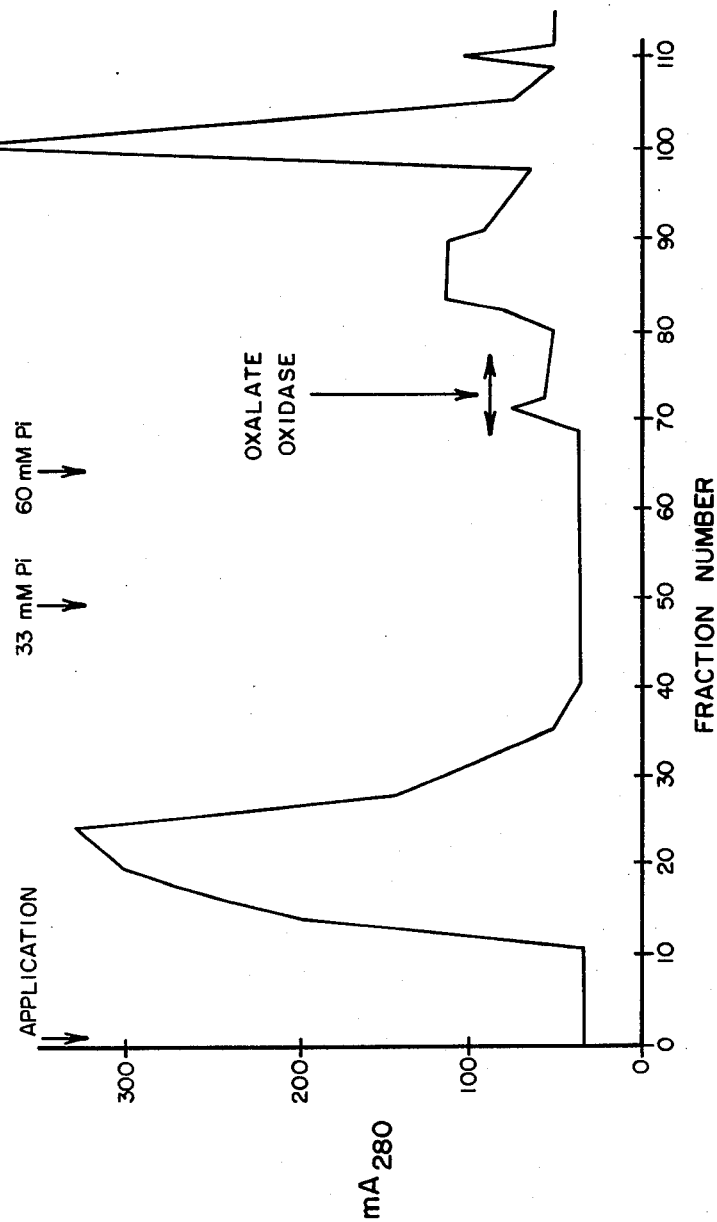
FIG. 1 is a graph illustrating the elution of instant oxalate oxidase from a hydroxyapatete column during the final chromatographic step in the purification of the enzyme.

As already noted, the instant oxalate oxidase composition may be extracted from the stems of beets. These stems are inexpensive and readily available in ton quantities, since during processing of beets only the beet itself is retained and the stems and other green parts of the plants are discarded as waste material. It is preferred to use the stems of the common beet, *Beta vulgaris*, although we believe that the stems of other beets, such as sugar beet, may also be employed. In the first step of the process for preparing the oxalate oxidase composition from the beet stems, the stems are finally divided, conveniently by means of any conventional blender, in an aqueous solution substantially isotonic with the cells in the stems. The preferred solution for use in this process is a sucrose solution having a concentration of about 0.5M. The solution, or rather pulp, produced from the finely divided stems is then filtered through a coarse filter, conveniently cheesecloth. To ensure maximum extraction of the oxalate oxidase from each batch of stems, it is advantageous to rehomogenize the pulp remaining on the cheesecloth and again filter it through cheescloth to produce further filtrate. The filtrate produced by the passage through the coarse filter is then centrifuged at at least about 10,000 g. for at least about 20 minutes; it is preferred to conduct the centrifuging at about 14,000 g. for about 30 minutes. This centrifuging causes a solid precipitate to form at the bottom of the tube, and the supernatant centrate is discarded. The precipitate is then suspended in a buffered sugar solution; the preferred solution is a 0.5 M sucrose solution buffered to pH 5.7 with 40 mM phosphate buffer. To this solution there is added a water-miscible organic solvent, preferably acetone. The organic solvent should be added in the cold in order to avoid any thermal degradation of the enzyme, and it has been found that adding about four parts by volume of acetone to about one part by volume of the sucrose solution containing the enzyme gives optimum results. The acetone solution is filtered and the residue dissolved, preferably in a 0.5M sucrose solution buffered to pH 5.7 with 20 mM phosphate buffer.

The next step in the isolation of the oxalate oxidase composition comprises adding taurodeoxycholic acid to the buffered sucrose solution containing the oxalate oxidase. Desirably, this acid is added in an amount of about one gram per 100 ml. of the solution and the solution then stirred for about 48 hours The major part of the oxalate oxidase remains in solution in the taurodeoxycholic acid solution, but some precipitate is formed and it desirable to remove this precipitate by centrifuging, conveniently at 30,000 g. for 30 minutes. However, since some oxalate oxidase is carried down with the precipitate, to ensure maximum yield of oxidase it is desirable to re-extract the resultant precipitate for about 24 hours with a 1% w/v taurodeoxycholic acid solution 0.5M in sucrose and buffered to pH 5.7 with a 40 mM phosphate buffer. The supernatant liquors from both extractions should then be combined and dialyzed against a buffer having a pH of about 5.7 to about 6.8; the preferred buffer is a 20 mM phosphate buffer of pH 5.7.

Following the dialysis, the solution may again be centrifuged and is then subjected to the final purification step, which comprises solid/liquid chromatography of the dialyzed solution using a buffer, preferably a 20 mM phosphate buffer of pH about 5.7 as the liquid phase. The acid phase used in this chromatographic step may be either hydroxyapatite (obtainable from Biorad Laboratories, 2200 Wright Avenue, Richmond, Calif. 94804) or a diethylaminoethyl anion exchange resin such as that which is commercially available under the trade name "DEAE-Sephacel" from Pharmacia Fine Chemicals, Uppsala, Sweden. The chromatography is preferably run at room temperature and it is desirable to increase the concentration of the phosphate buffer during the latter stages of the elution.

Because of the temperature sensitivity of the enzyme, all steps in the preparative process prior to the chromatography are desirably conducted at below ambient temperatures and preferably at about 4° C. Also, to prevent thermal degradation of the oxalate prior to its use in assay procedures, it is desirable to take the eluted fractions having the highest oxidase activity, make them 0.5M with sucrose and freeze them until they are to be used.

By the aforementioned procedure, approximately 45 International Units of oxalate oxidase can be extracted from 2,000 g. of beet stems; this is estimated to be about 10% of the oxalate oxidase originally present in the stems. The oxalate oxidase is obtained from the chromatography step in the form of a composition having an activity of at least about 5 units/mg. of protein in the composition. Compositions containing at least 9.5 units/mg. of protein are readily obtained, and by careful control of the preparative technique, compositions have been obtained containing about 17.6 units/mg. of protein. The effectiveness of the preparative technique already described in concentrating oxalate oxidase may be seen from the result of a typical experiment in which the solution (hereinafter referred to as the "stem preparation") formed by resuspending the precipitate from the first centrifugation in sucrose solution had a volume of 60 ml., an oxalate oxidase activity of 2.1 units/ml. and a protein concentration of 25.7 mg./ml., thus giving a specific activity of only 0.082 units/mg. of protein. In the same experiment, the solution formed after extraction with taurodeoxycholic acid had a volume of 82 ml., an activity of 0.47 units/ml. and a protein content of 0.6 mg./ml., and thus had a specific activity of 0.79 units/mg. of protein, representing a purification by a factor of 9.6 as compared to the stem preparation. The final preparation produced by chromatography in the same experiment had a volume of 50 ml. an activity of 0.42 units/ml. and a protein content of only 0.024 mg./ml., thus displaying a specific activity of 17.6 units/mg. of protein, representing a purification by a factor of 215 as compared by the stem preparation. The total amount of oxalate oxidase remaining in the final composition was 17% of that in the stem preparation. Thus, the final composition following chromatography contained only 57 $\mu$g. of protein per unit of oxidase activity and appeared to be substantially homogeneous under electrophoresis. The molecular weight of the oxidase, as determined by the method of Zwaan using polyacrylamide electrophoresis was 92,000 daltons and the composition had a Km. value of 0.6 mM with oxalate as substrate.

A detailed description of the extraction of the instant oxalate oxidase composition is given in our paper:

Obzansky, D. M., Ucchino, M., Richardson, K. E., Purification and characterization of an oxalate oxidase from been stems, Clin. Chem. 27(6), 1032 (1981);

the disclosure whereof is herein incorporated by reference.

As already mentioned, the oxalate oxidase composition has an optimum pH of about 5.7 and is thus preferably buffered to a pH in the range of about 5.5 to about 5.9. The activity of the oxalate oxidase is very highly specific when tested in a 57 mM phosphate buffer of pH 5.7 on various substrates in concentrations of 2.6 mM; under these conditions the instant oxalate oxidase compositions show an oxidase activity on citrate of only about 2% of their activity on oxalate and display no detectable oxidase activity on L-ascorbate, glyoxylate, glycolate, $\beta$-hydroxypyruvate, $\alpha$-ketoglutarate, succinate, adipic acid, suberic acid, L-methionine, L-glutamic acid, DL-mandelic acid, oxalacetic acid p-hydroxyphenylpyruvic acid, L-malic acid, L-cysteine, phenyllactic acid, acetylsalicylic acid, malonic acid, glutathione, acetoacetic acid, uric acid, pyruvic acid, creatinine, glycine, formic acid, urea, tartaric acid, hippuric acid phenylacetic acid,p-hydroxyphenylacetic acid or glucose.

To check the activation or inhibition of the instant oxalate oxidase compositions by various compounds, the activity of the compositions was measured in a 43 mM phosphate buffer at pH 5.7, containing 3.4 mM of oxalate and the activity was determined the quantity of carbon dioxide produced. At concentrations of 6.9 mM, both 8-hydroxyquinoline and flavin mononucleotide showed strong activation of the oxalate oxidase; the former compound produced an oxalate oxidase activity of 244% of the control solution containing the enzyme alone, whereas the latter compound produced an activity of 228% of the control. Flavin adenine dinucleotide at a concentration of 6.9 mM had no appreciable activity on the activity of the oxalate oxidase, while 1.0 mM of sodium chloride also did not inhibit the oxalate oxidase; in fact, this concentration of sodium chloride appeared to show a slight activation of the oxalate oxidase, the activity measured experimentally being 108% of that of the control. At a concentration of 100 mM, sodium chloride inhibited the activity of the oxalate oxidase by only 25%. These results with sodium chloride are especially significant when the oxalate oxidase is to be used for analyzing body fluids which often contain substantial concentrations of sodium and chloride; the moss and barley seedling oxalate oxidases hitherto used for this purpose are severly inhibited by sodium chloride concentrations as low as 1.0 mM and total inhibition (for practical purposes) of the prior art oxalate oxidases takes place at 100 mM concentration of sodium chloride. Accordingly, the use of the instant oxalate oxidase compositions in analysis of body fluid should lead to much more reliable results than those available using the oxalate oxidases from moss or barley seedlings, and will avoid the need for complicated purification of body fluids to remove sodium chloride before analysis.

In the instant method for estimating oxalate in a liquid, the instant oxalate oxidase is added to the liquid and converts the oxalate and oxygen present therein into carbon dioxide and hydrogen peroxide. The amount of oxalate originally present in the liquid may be determined by measuring any one or more of the oxygen and oxalate consumed, or the hydrogen peroxide and carbon dioxide produced, in this reaction. The oxalate consumed can be measured by adding a known quantity of $^{14}C$-labelled oxalate to the liquid and then measuring the amount of unlabelled oxalate originally present in the liquid by an isotope dilution method. The amount of oxygen consumed can be measured by an oxygen electrode. Although in theory the amount of carbon dioxide produced could be measured manometrically, in practice the amount of carbon dioxide involved is so small (one is typically concerned with analysis of body fluids containing no more than about 50 µg/ml. of oxalate) that manometric measurement of carbon dioxide does not give sufficiently accurate measurement, nor does measurement of the change in pH caused by the evolution of carbon dioxide. However, the carbon dioxide produced can be measured using a sensitive carbon dioxide electrode, such as that described in:

Kobos, R. K., and T. A. Ramsey, Anal. Chim. Acta, 121, 111–118 (1980). To obtain accurate oxalate determinations at the oxalate concentrations found in body fluids, we prefer to measure the hydrogen peroxide produced from the oxalate. Any method of estimating hydrogen peroxide of sufficient accuracy to measure hydrogen peroxide present in concentrations of a few milligrams per liter may be used to complete the assay. Appropriate techniques for measuring hydrogen peroxide in this concentration range including the use of hydrogen peroxide electrodes, have been described in the prior art, and we prefer to use a colorimetric method in which the hydrogen peroxide is allowed to react with an oxidizable chromogen in the presence of a peroxidase. (The peroxidase serves to catalyze the oxidation of the chromogen by the hydrogen peroxide.) The presently preferred chromogen/peroxidase combination is MBTH-DMA/horseradish peroxidase described above. Further details of the preferred technique for using this chromogen/peroxidase combination are given in the examples below.

Although, as stated above, the instant oxalate oxidase composition has no perceptible oxidase activity upon L-ascorbate (vitamin C), the presence of ascorbate in the sample to be assayed is undesirable since it does interfere in the MBTH-DMA/horseradish peroxidase hydrogen peroxide assay by inhibiting color formation. Small quantities of ascorbate are a normal constituent of mammalian urine and other body fluids, and much larger quantities of ascorbate are present in the urine of human beings who have been taking very large doses of ascorbate as vitamin supplements; certain individuals may take 2–3 grams of ascorbate per day in the belief that this reduces the risk of various infections, including the common cold. In addition large doses of vitamin C are sometimes administered intravenously for pharmaceutical purposes. Accordingly, when the sample being subjected to the oxalate assay is likely to contain ascorbate, this ascorbate should be removed before the assay, and such removal of ascorbate is conveniently effected by adding acidified ferric chloride to the liquid to be analyzed and thereafter passing the liquid through a cation exchange resin to remove ferric ion from the solution. However, since the removal of very large amounts of ascorbate may pose problems in accurately assaying the oxalate (as described in more detail below), and the removal of large amounts of ascorbate may itself introduce small quantities of oxalate into the specimens, it is preferred that a patient not take large doses of vitamin C for about 48 hours preceding the oxalate assay.

As illustrated in detail in the examples below, the preferred embodiment of the instant assay method can be effected by adding a single solution containing the oxalate oxidase, the MBTH-DMA chromogen and the horseradish peroxidase to the liquid to be assayed and then measuring the resultant color. Although the peroxidase requires a pH of about 4.1, whereas the optimum pH for the instant oxalate oxidase composition is about 5.7, the instant oxalate oxidase composition possesses sufficient activity at pH 4.1 to enable the analysis to be conducted without requiring a change of pH during the analysis.

Because the instant assay method can thus be conducted in a single step, it is well-suited to use in automatic analyzers of the type routinely used in medical laboratories. For example, we have found that by using the commercially available Abbott automatic analyzer model ABA-100 (obtainable from Abbot Laboratories, Diagnostic Division, 820 Mission Street, South Pasedena, Calif. 91030) it is possible to conduct 20 analyses by the instant method in about 20 minutes ABA analyzer time. This represents a great saving of laboratory technician time and cost as compared with the prior art methods using oxalate oxidases derived from moss or barley seedlings. The instant method is, as shown below, capable of giving very reliable results and can detect oxalate down to about 5 µg/ml.

The following examples are now given, though by way of illustration only, to show details of preferred compositions, preparative processes and assay methods of the instant invention.

EXAMPLE 1

This example illustrates the preparation of an oxalate oxidase composition from beet stems by the instant preparative method.

Stems were cut from common beet, Beta vulgaris, variety "greentop bunching", obtained from Holthouse Brothers, Route 2, Willard, Ohio 44890. 1,000 grams of the cut beet stems were washed, dried at room temperature and homogenized with 500 ml. of a 0.5M aqueous solution of sucrose in a blender. This and the subsequent steps were conducted at 4° C. unless otherwise stated, to avoid thermal degradation of the oxalate oxidase. The resultant solution was filtered through three layers of cheesecloth, the filtrate collected and the pulp remaining on the filter homogenized and refiltered in the same manner four more times. Exactly the same procedure was used to treat a further batch of 1,000 grams of beet stems. All the resulting filtrates were combined and centrifuged for 30 minutes at 14,000 g. The resultant precipitate was resuspended in 100 ml. of a 0.5M aqueous sucrose solution buffered to pH 5.7 with a 40 mM phosphate buffer. 400 ml. of cold (4° C.) acetone were added to the solution and the resulting acetone/water solution was quickly filtered through a sintered glass funnel.

The residue remaining on the filter was dissolved in a 0.5M aqueous sucrose solution buffered to pH 5.7 with a 20 mM phosphate buffer and sufficient taurodeoxycholic acid (obtained from Sigma Co., St. Louis, Mo. 63178) was added to the solution to give a concentration of the acid of 1 gram per 100 ml. of solution. The solution was stirred for 48 hours and then centrifuged at 30,000 g. for 30 minutes. The centrate was retained and the precipitate again extracted with a solution containing 1% w/v of taurodeoxycholic acid, 0.5M of sucrose and a 40 mM phosphate buffer (pH 5.7) for 24 hours, then the resulting solution was again centrifuged in the same manner. The two centrates were combined and dialyzed for 24 hours against 4 liters of a 20 mM phosphate buffer of pH 5.7, and the dialyzed solution again centrifuged at 30,000 g. for 30 minutes.

The dialyzed and centrifuged solution was then subjected to liquid/solid chromatography using as the solid phase the anion exchange resin commercially-available as DEAE-Sephacel from Pharmacia Fine Chemicals, Uppsala, Sweden. A column 5 cm. in diameter and 6.5 cm. in length was used and was equilibriated with a 20 mM phosphate buffer of pH 5.7 before use. The column chromatography was effected at room temperature with a flow rate of 1.0 ml/min., and the oxalate oxidase fraction was eluted with a 0-1M sodium chloride linear gradient in a 20 mM phosphate buffer of pH 5.7. The eluted fractions with the highest oxalate oxidase activity were pooled, made 0.5M in sucrose and frozen in 5 ml. aliquots. The yield of enzyme was approximately 45 International Units, representing approximately 10% of the enzyme originally present in the beet stems.

A further batch of enzyme was prepared from beet stems in substantially the same manner, except that the dialysis was conducted against 5 mM phosphate buffer of pH 6.8 and that the chromatography was conducted on hydroxyapatite using an 80 mM phosphate buffer of pH 6.8, the concentration of this buffer being altered during the run as shown in FIG. 1 below. The liquid leaving the column was collected in 10 ml. fractions and the absorption of each fraction at 280 nm. was measured. The results of this absorption analysis are shown in FIG. 1, which also shows that the oxalate oxidase is found in the fractions numbered from about 69 to about 78.

EXAMPLE 2

This Example illustrates the effect of pH on the oxidase activity of the instant composition.

Figure 2:
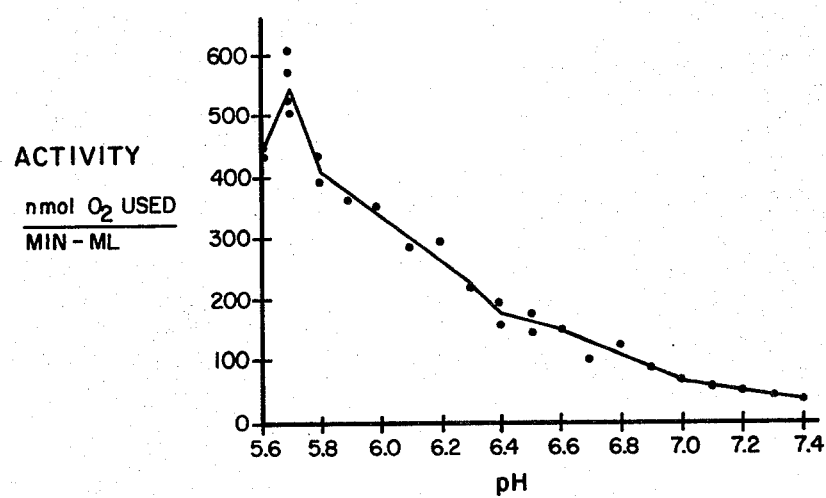
FIG. 2 is a graph illustrating the variation of the activity of the instant oxalate oxidase with pH.

The activity of the oxalate oxidase composition prepared by the second of the two procedures described in Example 1 above was determined by measuring the rate at which these preparations consumed oxygen when oxidizing a solution containing 5 mM of oxalate in a 54 mM phosphate buffer buffered to pH's in the range of 5.6 to 7.4. The results are shown in FIG. 2, which shows the nanomoles of oxygen used per minute per ml. of the solution for each unit of enzyme. It will be seen from FIG. 2 that the optimum pH of the enzyme is 5.7 and that the activity of the enzyme declines rapidly above about pH 5.9.

EXAMPLE 3

This Example illustrates the accuracy of oxalate determinations available by the instant assay method.

Figure 3:
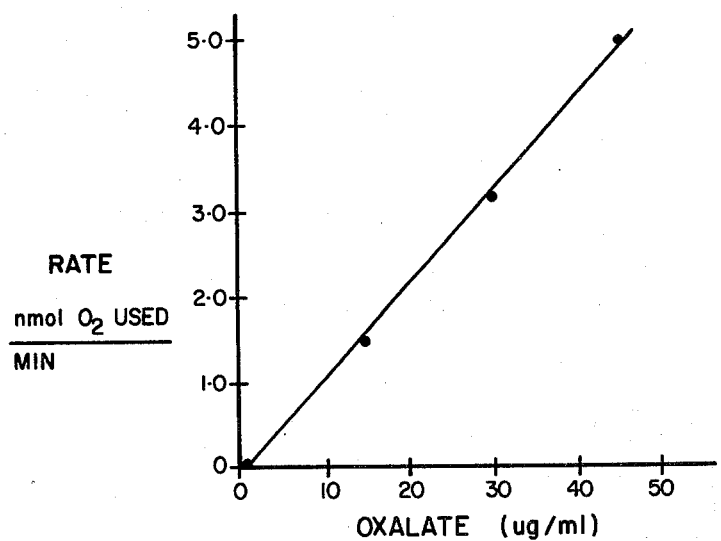
FIG. 3 is a calibration curve illustrating the accuracy of oxalate assay achievable by the instant method using an oxygen electrode.

Standard solutions containing 15, 30 and 45 $\mu$g/ml. of oxalate were prepared in separate experiments. 1 ml. of each of these standard oxalate solutions were mixed with 1 ml. of a 20 mM phosphate buffer, pH 5.7, containing 0.14 units of oxidase prepared in the manner described in the second part of Example 1. The rate of oxygen consumption of the mixed solutions was measured at 37° C. using a standard oxygen electrode obtained from Yellow Spring Instruments, Kettering, Ohio, and the results are shown in FIG. 3. It will be seen from this Fig. that the rate of oxygen consumption is substantially linearly related to the concentration of oxalate in the solution; in fact, the correlation coefficient between the oxalate concentration and the rate of oxygen consumption was 0.995.

EXAMPLE 4

This Example illustrates the use of the instant assay method to assay oxalate in urine.

Preparation of Reagents

In these experiments, the instant oxalate oxidase composition was used in combination with horseradish peroxidase (type I obtained from Sigma Chemical Co.) and the MBTH-DMA chromogen similar to that described in:

Gochman and Schmidt, J. M., Application of a new peroxide indicator reaction to the specific automated determination of glucose with glucose oxidase, Clin. Chem. 18(9), 943–950 (1972).

MBTH, obtained from Eastman Kodak Co., Rochester, N.Y. 14650 was made up into a 1 g/l. stock solution in 0.1M hydrochloric acid and stored in amber glass bottles at 4° C. Similarly, DMA, obtained from Fisher Scientific Co. Fairlawn, N.J. 07410, was made up into a 2.5 g/l stock solution in 0.1M hydrochloric acid and stored in the same manner. The assay reagent was prepared immediately before each use by combining 0.5 ml. of the stock MBTH solution, 1 ml. of the stock DMA solution, 13.5 ml. of 200 mM citrate buffer (pH 4.36; the acid present in the other solutions lowers the final pH of the mixed solution to the optimum value of 4.1), 0.6 ml (1500 IU) of the horseradish peroxidase and 5 ml. of the instant oxalate oxidase composition prepared as described in Example 1 and containing 0.5 units/ml. The combined solution was shielded from light with aluminum foil and warmed to room temperature before use.

Preparation of Standard and Control Solutions

A stock sodium oxalate solution, prepared from sodium oxalate, obtained from Allied Chemical, New York, N.Y., containing 893.44 mg. of sodium oxalate per liter (equivalent to 600 mg./l. of anhydrous oxalic acid) was diluted with water to 60 mg./l. of oxalic acid equivalent and stored at 4° C. Oxalic acid was added to pooled urine to produce controls with three different oxalate concentrations (14.6, 24.9 and 59.4 mg./L and these three controls were frozen in 5 ml. aliquots.

Analytical Procedure

In addition to the actual samples of urine being analyzed, one water blank, two separate 60 mg/l. oxalic acid standard solutions and three controls were carried through the entire analytical procedure. Two 5 ml. aliquots of the patients urine were pipeted into 16×150 mm. polystyrene tubes. 0.2 ml. of water were added to one tube and the same amount of 600 mg./l. oxalic acid equivalent standard were added to the second tube. The same amount of water was also added to the water blank, the oxalic acid standards and the three controls. There was then added to each tube 0.5 ml. of a 7.4 mM solution of ferric chloride in 3M hydrochloric acid and the tubes were heated to 60° C. for 30 minutes: this treatment with hot acidified ferric chloride served to destroy ascorbate in the solutions.

A cation exchange resin column was prepared by placing 1 gram (dry weight) of AG 50 W-X8 (100–200 mesh) cation exchange resin, obtained from Bio-Rad Laboratories, Richmond, Calif. 94804, into polypropylene Econo-Columns from the same manufacturer. The placing of the resin within the columns was effected by suspending 40 grams of the resin in 200 ml. of water and pipeting 5 ml. of the stirred suspension into each column, after which the resin within the column was blown dry by passing nitrogen therethrough.

4 ml. of the urine treated by the acid ferric chloride treatment were poured onto the resin and the effluent discarded. Thereafter, a further 1 ml. of urine was poured onto the resin and the effluent collected. This treatment of the urine with cation exchange resin served to remove ferric ion from the urine.

An Abbott ABA-100 automatic analyzer was set up with the parameters described in the following table:

TABLE 1

| PARAMETERS FOR THE ABBOTT ABA-100 | |
| --- | --- |
| Decimal point: | 000.0 |
| Incubator: | 37 |
| Mode: | end point |
| Reaction direction: | down |
| Analysis time: | 20' |
| Carousel revolution: | 2 |
| Course: | 1 |
| Filter: | 500/600 |
| Syringe plate: | 1:26 |

50 microliters of the collected effluent were placed in each cup of the analyzer and the instrument run in the normal manner. The instrument was zeroed with the water blank and calibrated with the 60 mg/l. standards.

The recovery of oxalic acid from the urine of each patient was calculated from the formula:

$R = (B - A)/24$ where:

B is the oxalic acid content in mg/l. in the tube with 0.2 ml of 600 mg/l oxalic acid equivalent standard added; and A is the oxalic acid concentration in mg/l. in the tube with 0.2 ml. of water added.

The parameter 24 is of course derived from the concentration 24 mg/l. of oxalic acid added.

The number of milligrams of oxalic acid excreted per day by each patient is given by:

excreted oxalic acid = $AV/R$ where V is the volume of urine in liters excreted by the patient in 24 hours.

Results

Table 2 below shows that the instant assay method provides excellent reproducibility both within runs and between runs conducted in consecutive days.

TABLE 2

| N | mg/l. (mM) oxalic acid | | CV, % |
| --- | --- | --- | --- |
| | MEAN | SD | |
| | WITHIN - RUN | | |
| 29 | 13.2 (0.15) | 0.15 (0.002) | 1.1 |
| 29 | 23.1 (0.26) | 0.36 (0.004) | 1.5 |
| 29 | 53.3 (0.59) | 0.36 (0.004) | 0.7 |
| | BETWEEN - DAY | | |
| 20 | 14.6 (0.16) | 0.76 (0.008) | 5.2 |
| 20 | 24.9 (0.28) | 1.38 (0.015) | 5.5 |
| 20 | 59.4 (0.66) | 2.61 (0.029) | 4.4 |

Recovery of oxalate from the urine was assessed by a series of experiments in which increasing concentrations of oxalate were added to patients urine. The results are shown in Table 3. In this table, the recovery factors for oxalic acid corrected by use of the internal standard are determined by dividing the measured concentration by the factor R defined above. The recovery factor by the internal standard method was 0.9304.

TABLE 3

| RECOVERY OF OXALIC ACID ADDED TO URINE | | | | |
| --- | --- | --- | --- | --- |
| oxalic acid mg/l. | | oxalic acid recovered and % recovery (uncorrected) | | internal standard corrected oxalic acid recovered and % recovery |
| added | found | mg/l. | % | mg/l. | % |
| 0.0 | 17.8 | | | | |
| 12.0 | 28.8 | 11.0 | 91.7 | 11.8 | 98.5 |
| 24.0 | 40.0 | 22.2 | 92.7 | 23.9 | 99.6 |
| 36.0 | 51.3 | 33.5 | 93.0 | 36.0 | 100.0 |
| 48.0 | 60.7 | 42.9 | 89.5 | 46.2 | 96.2 |
| 60.0 | 70.9 | 53.1 | 88.6 | 57.1 | 95.2 |
| AVERAGE RECOVERY, % (SD) | | | 91.1 (1.9) | | 97.9 (2.1) |

The data in Table 3 show that when the oxalic acid concentration is not corrected by the internal standard, the recovery factor is less than 90% but that when an internal standard correction is used, recovery is greater than 95%. The data in Table 3 also showed that the instant assay method is linear to 70 mg/l. and sensitive down to at least 5 mg/l.

Figure 4:
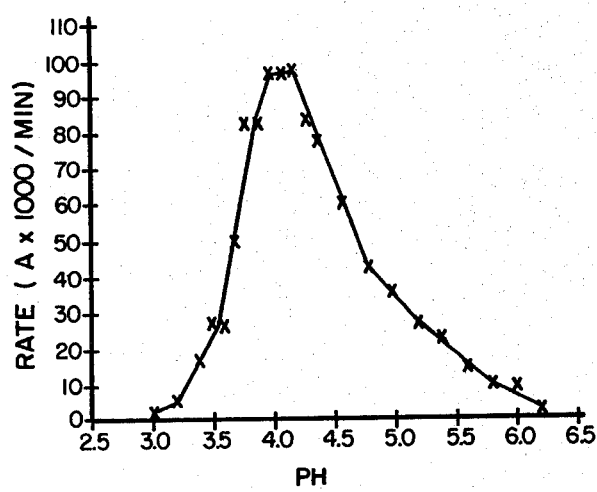
FIG. 4 is a graph illustrating the variation of the rate of the oxalate oxidase/horseradish peroxidase coupled reaction used in the instant assay method with pH.

A separate series of experiments were undertaken to determine the effect of pH on the rate of coupled enzymatic reaction used in the assay procedure, using specimens of the chromogen reagent having varying pH values but constant ionic strengths. FIG. 4 shows that the maximum rate of the coupled reaction occurs at pH 4.1, which is close to the optimum pH for the horseradish peroxidase and, although considerably lower than the optimum pH for the oxalate oxidase, is still high enough for the oxalate oxidase to possess activity sufficient for practical purposes.

Table 4 below shows the results of series of experiments in which various organic compounds likely to be found in human body fluids were added to the urine before the oxalic acid assay. Besides the compounds specifically mentioned in Table 4, glycolate, β-hydroxypyruvate, α-ketoglutarate, succinate, adipic acid, suberic acid, L-methionine, L-glutamic acid, DL-mandelic acid, p-hydroxyphenylpyruvic acid, L-malic acid, phenyllactic acid, acetylsalicylic acid, malonic acid, acetoacetic acid, uric acid, creatinine, glycine, formic acid, urea, tartaric acid, hippuric acid, phenylacetic acid, p-hydroxyphenylacetic acid and glucose were tested and found to have no effect on the assay results. As shown in this table, the only one of the compounds tested which significantly interferes with the oxalate assay at concentrations which are likely to be present in body fluids is ascorbic acid at concentrations of 2.5 mM (440 mg/l.), or greater; although glutathione significantly interferes at a concentration of 5.0 mM, this is considerably higher than is likely to be encountered in practice in the analysis of body fluids. By using the 24 mg/l. oxalic acid internal standard, urines with significant interfering compounds could be noted. In two patients receiving intravenous ascorbic acid, the uncorrected recovery factors for oxalate were less than 70%. Accordingly, patients should be instructed to discontinue ascorbic acid ingestion prior to oxalic acid assay, both because the ascorbate interferes with the oxalate analysis and because ascorbic acid is metabolized to oxalic acid in vivo.

TABLE 4

| | INTERFERENCE STUDY | | |
|---|---|---|---|
| Test compound | Concentration mM | Oxalic acid found mg/l. | % of control |
| Control | no addition | 45.3 | 100% |
| L-cysteine | 5.0 | 42.0 | 92.7 |
| | 2.5 | 43.8 | 96.7 |
| | 0.5 | 45.3 | 100.0 |
| oxalacetic acid | 5.0 | 43.5 | 96.0 |
| | 2.5 | 43.8 | 96.7 |
| | 0.5 | 44.7 | 98.7 |
| glyoxylic acid | 5.0 | 39.8 | 87.8 |
| | 2.5 | 42.7 | 94.3 |
| | 0.5 | 44.6 | 98.5 |
| glutathione | 5.0 | 35.9 | 79.2 |
| | 2.5 | 39.4 | 87.0 |
| | 0.5 | 44.0 | 97.1 |
| Pyruvic acid | 5.0 | 44.4 | 98.0 |
| | 2.5 | 45.0 | 99.3 |
| | 0.5 | 45.4 | 100.2 |
| ascorbic acid | 5.0 | 0.0 | 0.0 |
| | 2.5 | 38.7 | 85.4 |
| | 0.5 | 43.9 | 96.9 |

As mentioned above, the acidic ferric chloride treatment is intended to remove interfering ascorbate. To determine if the acidic ferric chloride treatment produced any oxalic acid, and thus introduced spurious results, ten samples of urine were incubated with oxalate decarboxylase for four days at 37° C.; the final concentrations of the components of the oxalate decarboxylase solution components in the treated solution were 0.005 International Units of oxalate decarboxylase and 6.8 mM of ethylenediaminetetraacetic acid in a 0.4M citrate buffer of pH 3.0. The decarboxylated urine samples were then subjected to the acid ferric chloride treatment and the remainder of the oxalate acid procedure described above. As shown in Table 5 below, the results indicate that no significant amount of oxalate is produced during the acid ferric chloride treatment.

TABLE 5

| OXALIC DECARBOXYLASE TREATED URINE | | |
|---|---|---|
| Sample number | mg/l. oxalic acid | |
| | before OD treatment | after OD treatment |
| 1 | 27.1 | 0.8 |
| 2 | 24.2 | 0.6 |
| 3 | 9.3 | 0.0 |
| 4 | 27.3 | 0.0 |
| 5 | 8.6 | 0.4 |
| 6 | 7.0 | 0.2 |
| 7 | 11.7 | 0.4 |
| 8 | 13.6 | 0.2 |
| 9 | 12.1 | 0.4 |
| 10 | 14.0 | 0.6 |

The oxalate assays produced by the instant method were compared with a variety of prior art methods, and especially with a radioenzymatic method involving the precipitation of calcium oxalate followed by ether extraction, the extracted oxalate acid subsequently being determined by isotope dilution with oxalate decarboxylase and with the chromotropic acid method described in:

Hodgkinson, A. and Williams, A., An improved colorimetric procedure for urine oxalate, Clin. Chim. Acta 36, 127–132 (1972).

Figure 5:
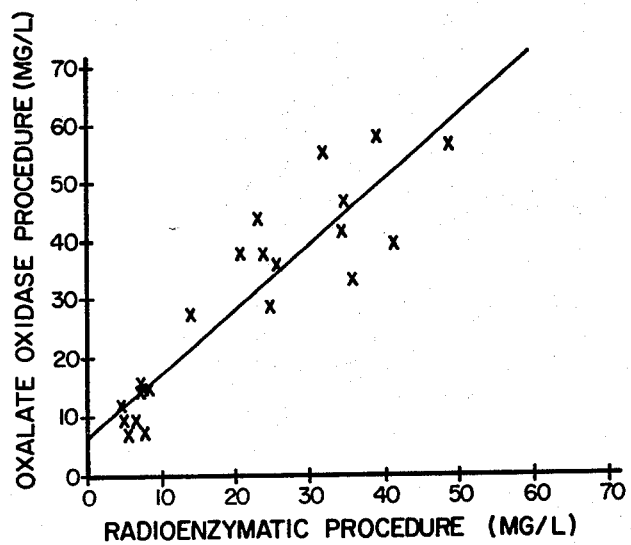
FIG. 5 is a graph illustrating the comparative oxalate assay results obtained by the instant assay method and a prior art radioenzymatic method.
Figure 6:
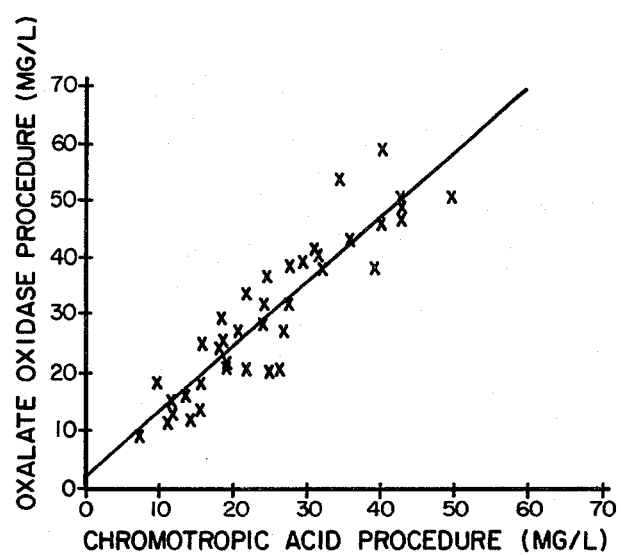
FIG. 6 is a graph illustrating the comparative oxalate assay results obtained by the instant assay method and the prior art chromotropic acid method.

The results obtained from individuals using the radioenzymatic method and the instant method are shown in Table 6 below and are plotted graphically in FIG. 5, while the results obtained when comparing the chromotropic acid method and the instant method are shown in Table 7 below and are plotted graphically in FIG. 6. In both cases, the results obtained by the instant method are similar to those obtained by the prior art method (the correlation coefficient for the instant method results against those obtained by the chromotropic acid method is 0.9168), although the instant method is of course much more convenient.

TABLE 6

| COMPARATIVE METHOD DATA - RADIOENZYMATIC METHOD VS OXALATE OXIDASE METHOD | |
|---|---|
| RADIOENZYMATIC METHOD (mg/L) | OXALATE OXIDASE METHOD (mg/L) |
| 24.0 | 37.4 |
| 14.1 | 27.5 |
| 6.6 | 9.4 |
| 24.7 | 28.7 |
| 4.9 | 8.9 |
| 5.5 | 6.7 |
| 7.6 | 7.0 |
| 8.4 | 14.5 |
| 7.4 | 15.4 |
| 4.5 | 11.7 |
| 7.2 | 14.0 |
| 39.5 | 57.8 |
| 32.2 | 55.5 |
| 41.8 | 39.4 |
| 49.2 | 56.2 |
| 20.9 | 37.9 |
| 35.9 | 32.9 |
| 25.8 | 35.7 |
| 34.8 | 46.6 |
| 34.6 | 41.4 |
| 23.2 | 43.4 |

TABLE 7
COMPARATIVE METHOD DATA - CHROMOTROPIC ACID VS OXALATE OXIDASE

| CHROMOTROPIC ACID METHOD, X mg/L | OXALATE OXIDASE METHOD, Y mg/L |
|---|---|
| 9.9 | 18.6 |
| 26.4 | 20.8 |
| 14.38 | 12.1 |
| 11.6 | 14.8 |
| 7.4 | 9.5 |
| 11.7 | 12.8 |
| 20.7 | 27.0 |
| 15.6 | 13.3 |
| 18.2 | 24.2 |
| 13.6 | 16.2 |
| 19.2 | 21.7 |
| 32.3 | 38.0 |
| 15.6 | 18.4 |
| 22.0 | 20.7 |
| 11.4 | 11.7 |
| 24.98 | 20.1 |
| 34.6 | 53.6 |
| 40.5 | 58.7 |
| 29.6 | 39.4 |
| 39.3 | 38.1 |
| 43.0 | 46.8 |
| 42.8 | 50.2 |
| 31.7 | 40.2 |
| 36.0 | 43.1 |
| 27.9 | 38.6 |
| 40.4 | 46.1 |
| 49.7 | 50.3 |
| 43.0 | 48.5 |
| 40.4 | 45.7 |
| 18.6 | 23.7 |
| 27.0 | 27.1 |
| 19.2 | 21.1 |
| 15.9 | 24.8 |
| 24.2 | 31.6 |
| 21.8 | 33.6 |
| 24.2 | 32.1 |
| 24.16 | 28.5 |
| 27.7 | 31.8 |
| 31.0 | 41.3 |
| 18.6 | 25.5 |
| 18.6 | 29.5 |
| 24.7 | 36.7 |

The results obtained by comparing with a variety of prior art oxalate assay methods are shown in Table 8 below. The population used for this study consisted of males and females between the ages of 20 and 35 who were on an unrestricted diet. The urine was collected without a preservative and assayed within 48 hours after collection. Again, the oxalate values found by the instant method compare favorably with the radioenzymatic method, which should in theory be the most accurate of the prior art methods, but is higher than in prior art enyzmatic methods.

TABLE 8
REFERENCE RANGES FOR URINARY OXALIC ACID BY VARIOUS METHODS

| Number of Subjects | Method | Oxalate output (mg/day) Mean | Range | Source |
|---|---|---|---|---|
| 12 M | colorimetric | 30.9 | 17.2–43.1* | a |
| 10 F | colorimetric | 30.7 | 24.1–46.8* | a |
| 20 | colorimetric | 31.0 | 15.0–50.0* | b |
| 8 | gas chromatography | 35.6 | 15.1–51.8* | c |
| 27 | isotope dilution | 29.4 | 18.0–47.0* | d |
| 11 M | isotope dilution | 33.0 | 24.0–49.3* | e |
| 5 F | isotope dilution | 35.1 | 21.8–44.8* | e |
| 4 | enzyme (oxidase) | 37.7 | 28–43* | f |
| 104 | enzyme (oxidase-ADH) | 18.4 | 7.5–32.9*** | g |
| 22 | enzyme (OD-FDH) | 25.9 | 14.0–37.6* | h |
| 22 | enzyme (OD-FDH) | 33.0 | 18.0–47.0 | i |
| 25 | enzyme (OD) | 20.5 | 4.7–36.3** | j |
| 23 | instant enzyme | 33.8 | 22.9–46.1 | this study |

M = male, F = female, * = extreme values,  = mean ± 2SD, * = 95% quantile, OD = oxalate decarboxylase, FDH = formate dehydrogenase.

a Hodgkinson, A. and Williams, A., An improved colorimetric procedure for urine oxalate, Clin. Chim. Acta 36, 127–132 (1972).
b Dempsey, E. F., Forbes, A. P., Melick, R. A. and Henneman, P. H. Urinary oxalate excretion, Metanolism 9, 52–58 (1960)
c Tocco, D.J., Duncan, A. E. W., Noll, R. M. and Duggan, D. E., An electroncapture gas chromatorgraphic procedure for the estimation of oxalic acid in urine, Anal. Biochem 94, 470 (1979).
d Hockaday, T. D. R., Frederick, E. W. Clayton, J.E. and Smith, J. E. N. Studies on Primary Hyperoxaluria II. Urinary Oxalate, Glycolate and Glyoxylate measurement by Isotope Dilution Methods J. Lab. & Clin. Med. 69 (4) 677–687 (1965);
e Gibbs, D. A. and Watts, R. W. E., The variation of urinary oxalate excretion with age; J. Lab. Clin. Med. 73(6), 901–908, (1969).
f Laker, M. F., Hofmann, A. F. and Meeuse, B. J. D., Spectrophotometirc determination of urinary oxalate with oxalate oxidase, Clin Chem. 26(7), 827–830(1980);
g Butz, M. and Kohlbecker, G. Oxalate urolithiasis; Significance of serum and urinary oxalate, Urol. Int. 35, 303–308 (1980).
h Costello, J., Hatch, M. and Bourke, E., An enzymic method for the spectrophotometric determination of oxalic acid, J. Lab. Clin. Med. 87(5), 903–908, (1976)
i Yriberri, J. and Posten, L. S., A semi-automatic enzymic method for investigating urinary oxalate, Clin. Chem., 26(7), 881–884 (1980);
j Mayer, G. G., Markow, D. and Karp, F. Enzymatic oxalate determination in urine.

Thus, it will be seen that the instant method provides a method for oxalate assay whose accuracy compares very favorably with prior art methods, which gives highly reproducible results, and which is less time consuming and expensive than prior art methods.

It will be apparent to those skilled in the art that numerous changes and modification may be made in the embodiments of the invention described above without departing from the scope thereof. Accordingly, the foregoing description is to be construed in an illustrative and not in a limitative sense, the scope of the invention being defined solely by the appended claims.

We claim:

1. An oxalate oxidase composition having an activity of at least about 5 international enzyme units/mg. of protein at 37° C. in said composition, said composition comprising an oxalate oxidase having an optimum pH of about 5.7, having an oxidase activity on citrate of only about 2% of its oxidase activity on oxalate, having substantially no oxidase activity on L-ascorbate, glyoxylate, glycolate, β-hydroxypyrovate, 2-ketoglutarate or succinate and not being inhibited by 1.0 mM sodium chloride solution.

2. A composition according to claim 1 wherein said oxalate oxidase is derived from the stems of beet.

3. A composition according to claim 1 having an activity of at least about 9.5 international units/mg.

4. A composition according to claim 2 having an activity of about 17.6 international units/mg.

5. A composition according to claim 4 wherein said composition contains not more than about 5.7 μg of protein per international unit of activity.

6. A composition according to claim 1 buffered to a pH in the range of about 5.5 to about 5.9.

7. A process for the preparation of an oxalate oxidase composition having an activity of at least about 5 international enzyme units/mg. of protein at 37° C. in said composition, said composition comprising an oxalate oxidase having an optimum pH of about 5.7, having an oxidase activity on citrate of only about 2% of its oxidase activity on oxalate, having substantially no oxidase activity on L-ascorbate, glyoxylate, glycolate, β-hydroxypyrovate, 2-ketoglutarate or succinate and not being inhibited by 1.0 mM sodium chloride solution which process comprises the following steps:

(a) finely dividing beet stems in an aqueous solution substantially isotonic with the cells of said stems;

(b) filtering the solution produced in step (a) through a coarse filter;

(c) centrifuging the filtrate produced in step (b) until a precipitate forms;

(d) suspending the precipitate formed in step (c) in an aqueous sugar solution;

(e) adding a water-miscible organic solvent to the suspension formed in step (d), thereby causing precipitation of an oxalate-oxidase-containing precipitate;

(f) dissolving the precipitate formed in step (e) in an aqueous solution containing taurodeoxycholic acid;

(g) dialyzing the solution formed in step (f) against a buffer solution having a pH of about 5.7 to about 6.8; and (h) chromatographing the dialyzed solution from step (g) by solid/liquid chromatography using a buffer of pH about 5.7 as the liquid phase.

8. A process according to claim 7 wherein said best stems used in step (a) are stems of *Beta vulgaris*.

9. A process according to claim 7 wherein said substantially isotonic solutions is a sucrose solution having a concentration of about 0.5M.

10. A process according to claim 7 wherein said filter used in step (b) is a cloth filter.

11. A process according to claim 7 wherein, the step (c), said centrifuging is conducted at at least about 10,000 g for at least about 20 minutes.

12. A process according to claim 11 wherein said centrifuging is conducted at about 14,000 g for about 30 minutes.

13. A process according to claim 7 wherein, step (d), said aqueous sugar solution comprises a sucrose solution having a concentration of about 0.5M buffered to about pH 5.7 with a phosphate buffer.

14. A process according to claim 7 wherein, in step (e), said water-miscible organic solvent is acetone.

15. A process according to claim 7 wherein, in step (f), said taurodeoxycholic acid solution has a concentration of about 1% by weight, is about 0.5M in sucrose and is buffered to about 5.7.

16. A process according to claim 7 wherein said chromatography is conducted on a hydroxyapatite solid phase and said liquid phase is a phosphate buffer.

17. A method for estimating oxalate in a liquid, which method comprises:

adding to said liquid an oxalate oxidase, said oxalate oxidase having an optimum pH of about 5.7, having an oxidase activity on citrate of only about 2% of its oxidase activity on oxalate, having substantially no oxidase activity on L-ascorbate, glyoxylate, glycolate, β-hydroxypyruvate, α-ketoglutarate or succinate and not being inhibited by 1.0 mM sodium chloride, thereby converting oxalate and oxygen present in said liquid to hydrogen peroxide and carbon dioxide; and assaying at least one of the oxalate or oxygen consumed, or hydrogen peroxide and carbon dioxide produced, by said oxalate oxidase, thereby determining the concentration of said oxalate in said liquid.

18. A method according to claim 17 wherein said oxalate oxidase is derived from the stems of beet.

19. A method according to claim 17 wherein, before said oxalate assay, said liquid is treated to remove ascorbate therefrom.

20. A method according to claim 19, wherein said removal of ascorbate is effected by adding acidified ferric chloride solution to said liquid and thereafter passing said liquid through a cation exchange resin to remove ferric ion therefrom.

21. A method according to claim 17 wherein said hydrogen peroxide produced by said oxalate oxidase is assayed.

22. A method according to claim 21 wherein said hydrogen peroxide assay is effected by means of a peroxidase and an oxidizable chromogen.

23. A method according to claim 22 wherein said peroxidase is horseradish peroxidase and said chromogen in MBTH-DMA.

* * * * *